(12) United States Patent
Sardo

(10) Patent No.: US 9,072,306 B2
(45) Date of Patent: Jul. 7, 2015

(54) METHOD FOR THE PRE- OR POST-HARVEST TREATMENT OF PLANT PRODUCTS, USING PHOSPHONIC ACID AND AN ESSENTIAL OIL

(75) Inventor: Alberto Sardo, Chateaurenard (FR)

(73) Assignee: XEDA INTERNATIONAL, Saint Andiol (FR)

( * ) Notice: Subject to any disclaimer, the term of this patent is extended or adjusted under 35 U.S.C. 154(b) by 123 days.

(21) Appl. No.: 13/824,653

(22) PCT Filed: Nov. 24, 2011

(86) PCT No.: PCT/EP2011/070912
§ 371 (c)(1),
(2), (4) Date: May 20, 2013

(87) PCT Pub. No.: WO2012/069576
PCT Pub. Date: May 31, 2012

(65) Prior Publication Data
US 2013/0236562 A1    Sep. 12, 2013

(30) Foreign Application Priority Data

Nov. 24, 2010 (FR) ...................... 10 59693

(51) Int. Cl.
| | |
|---|---|
| A01N 59/26 | (2006.01) |
| A23B 7/154 | (2006.01) |
| A23B 7/157 | (2006.01) |
| A01N 27/00 | (2006.01) |
| A01N 61/00 | (2006.01) |

(52) U.S. Cl.
CPC ............... *A01N 59/26* (2013.01); *A23B 7/154* (2013.01); *A23B 7/157* (2013.01); *A01N 27/00* (2013.01); *A01N 61/00* (2013.01)

(58) Field of Classification Search
CPC ....... A01N 59/26; A01N 61/00; A01N 27/00; A01N 31/16; A01N 65/00; A01N 2300/00; A23B 7/154; A23B 7/157
See application file for complete search history.

(56) References Cited

U.S. PATENT DOCUMENTS

| | | | |
|---|---|---|---|
| 4,075,324 A | 2/1978 | Thizy et al. | |
| 5,679,351 A | 10/1997 | Walter et al. | |
| 5,997,910 A | 12/1999 | Taylor | |
| 2008/0145499 A1* | 6/2008 | Sardo | ............................ 426/335 |
| 2008/0175926 A1 | 7/2008 | Bompeix et al. | |
| 2008/0248128 A1 | 10/2008 | Sardo | |

FOREIGN PATENT DOCUMENTS

| | | |
|---|---|---|
| FR | 2 819 992 | 8/2002 |
| FR | 2 867 026 | 9/2005 |
| FR | 2 913 177 | 9/2008 |
| JP | 60 146803 | 8/1985 |

OTHER PUBLICATIONS

International Search Report for PCT/EP2011/070912 dated May 16, 2012.
Database WPI Week 198537, Thomson Scientific, London, GB; AN 1985-226603, XP002637119, & JP 60 146803 A (Satsukime K) (Aug. 2, 1985) abstract.
Corsi G et al: "Biological and phytochemical aspects of Valeriana officinalis", Biochemical Systematics and Ecology, Pergamon Press, GB, vol. 12, No. 1, (Jan. 1, 1984), pp. 57-62.
Baranauskiene R:"Essential oil composition of Valeriana officinalis ssp. officinalis grown in Lithuania", Chemistry of Natural Compounds, Kluwer Academic Publishers-Consultants Bureau, NE, vol. 43, No. 3, (May 1, 2007), pp. 331-333.

* cited by examiner

*Primary Examiner* — Sean Basquill
(74) *Attorney, Agent, or Firm* — B. Aaron Schulman, Esq.; Stites & Harbison, PLLC

(57) ABSTRACT

The invention relates to the pre- or post harvest fungicidal and/or bactericidal treatment of plant products, using at least phosphonic acid that is at least partially salified and eugenol or clove oil, at ambient temperature, as well as to the compositions suitable for said method.

18 Claims, No Drawings

METHOD FOR THE PRE- OR POST-HARVEST TREATMENT OF PLANT PRODUCTS, USING PHOSPHONIC ACID AND AN ESSENTIAL OIL

The present invention relates to a method for the pre or post harvest treatment plant products. It is important that fruits and vegetables do not lose their organoleptic quality and retain an appealing appearance when placed on the market so as to ensure their rapid consumption. The phenomena that are likely to alter the appearance and the taste of the fruits and vegetables are in particular the proliferation of fungi and bacteria on their surface, which may occur during the cultivation and/or post harvest. Such deterioration and damage caused set in even faster in terms of tiny cuts, bruises and nicks appearing on the skin during storage for relatively long periods before being placed on the market or in the handling of fruits and vegetables. Another phenomenon that can damage fruits and vegetables, and plants under cultivation, is the phenomenon of scalds which is manifested by darkening of the skin of fruits and vegetables so affected.

Phosphonic acid ($H-PO_3H_2$) (PA) is also known as phosphorus acid ($H_3PO_3$). The activity of the PA is best known on mildew (Phycomycetes). In contrast, with respect to ascomycetes and imperfect fungi that are parasites of fruit and vegetables (*Fusarium* spp, *Botrytis* sp, *Phlyctema* sp, *Penicillium* spp, etc), PA has little effect. Nevertheless, attempts have been made to apply PA in post harvest treatment. Indeed, the permissible maximum residue limits (MRLs) (expressed in PA) after treatment on several crops are between 25 and 50 ppm: therefore post-harvest treat could be possible with relatively high doses. By way of comparison, the MRL for Pyrimethanil for the same crops is between 5 and 10 ppm. Unfortunately, at ambient temperature, activity is very weak, in particular on Penicilliums, even with treatment doses close to 10,000 ppm in particular in the case of Penicilliums in oranges.

However it is known that increasing the temperature of the treatment solution significantly increases the performance of various fungicides, especially when temperatures exceed 40° C. Thus, in the patent application EP 1 941 802 a new method has been described for the treatment of fruits and vegetables by means of phosphonic acid and eugenol, by applying this combination at a temperature between 30° C. and 60° C. However, this application at high temperatures is not easy to implement, involves various constraints, should be and is usually performed by immersion (dipping) and is not suitable for spraying. Thus, this treatment is in fact not very amenable to in orchard treatment. EP 1 941 802 describes only the activity on *Penicillium* and does not report any results with regard to resultant activity for the method when carried out at ambient temperature.

In practice, it turns out that phosphonic acid and eugenol demonstrate activity generally under high temperature, that is of a broad spectrum, but of low intensity which is thus considered insufficient in daily practice.

It is therefore desirable to provide a novel method for the treatment of plants under cultivation, fruit and vegetables at ambient temperature.

Thus, the present invention relates to a method for the pre- or post-harvest treatment of plant products that consists of the application of:
a form of phosphonic acid that is at least partially salified, and
an essential oil or one or more terpene agent(s) contained therein, and/or mixtures thereof,
at ambient temperature.

With regard to essential oils, mention may be made of clove oil, thyme oil, oregano oil, cinnamon oil, and peppermint oil, and as regards terpene agents, these include eugenol, isoeugenol, L-carvone, thymol, geraniol, carvacrol, cinnamaldehyde, and mixtures thereof.

In the above discussion as well as in the following sections, clove oil and/or eugenol, isoeugenol and mixtures thereof may in particular be mentioned.

The at least partially salified form of phosphonic acid may be a monophosphite (a molecule of phosphite $H-PO_3H^-$), a diphospite ($H-PO_3^{2-}$) or a sesquiphosphite ($H-PO_3H_{0.5}^{1.5-}$) with a metal cation, such as an alkali metal ($Na^+$ or $K^+$) or alkaline earth ($Ca^{2+}$, $Mg^{2+}$). Thus the phosphonic acid salt suitable for the method according to the invention corresponds to the general formula:

$$H_xM_yPO_3$$

wherein:
M represents a metal atom, in particular an alkali metal or alkaline earth metal, or an ammonium group or an amino group,
x is between 1 and 2.8, in particular between 1 and 2.5, especially between 1.3 and 1.7,
y is between 0.2 and 2, in particular between 0.5 and 2, especially between 1.3 and 1.7 and x+y=3.

Particularly preferable is the salt $H_{1.5}M_{1.5}PO_3$ with M=potassium for example.

Particularly preferable are the salts of alkali metal or alkaline earth and particularly the potassium salts of phosphonic acid and particularly potassium sesquiphosphite.

The phosphonic acid salt may be prepared in advance or formed in situ in the treatment composition. It is usually prepared or formed by reaction between phosphonic acid and the corresponding base, such as KOH, for example, the amount of base being appropriate to the desired salt.

In the foregoing and in the following sections, the terms "at least partially salified form of phosphonic acid" and "phosphonic acid salt" could be used in an interchangeable manner and refer to the previously prepared salt or to the salt that is in fact formed in situ.

The invention therefore also relates to a method for pre or post harvest treatment of plant products consisting of the application of:
phosphonic acid,
a base and
an essential oil or one or more terpene agent(s) contained therein, and/or mixtures thereof,
at ambient temperature.

The treatment according to the invention is particularly suitable for fungicidal and/or bactericidal treatment. It is particularly effective against the fungi *Phytophthora, Monilia, Penicillium* sp, *Geotrichum* sp, *Rhizoctonia, Helminthosporium, Colletotrichum*, and in particular *Geotrichum candidum, Rhizoctonia, Helminthosporium solani* and *Colletotrichum gloeosporioides*.

The term "pre or post harvest plant products" refers to plants under cultivation as well as to fruits or vegetables unpicked on stalks or harvested.

The treatment may be carried out in the orchard and or in the post harvest phase, by using known methods. Thus, the application of the treatment composition may be carried out by any known means, such as by spraying the plant products pre or post harvest or by the dipping of fruits and vegetables in the treatment solution maintained.

The fruits and vegetables may also be treated when they are stored in crates or on pallets, or even without crates or pallets, prior to being marketed, as is the case for example, for oranges.

More preferably, when fruits and vegetables in crates or on pallets are treated by dipping, the treatment composition may be applied by means of a device as described in patent application FR 01 096 27, or EP 1 941 802. These devices are particularly advantageous in that they allow uniform application of the solution on the fruits and vegetables stored on pallet or in crate.

The treatment, however, is more particularly suitable for treatment in the orchard, by means of spraying at ambient temperature.

The quantity of product applied generally depends on the quantity of pre or post harvest plant products to be treated, as well as on the conditions of storage and the actual and/or desired degree of maturity of fruits or vegetables stored.

Generally, the application doses of essential oil or one or more terpene agent(s) contained therein, and/or mixtures thereof, are between 300 ppm and 4500 ppm, and especially between 500 ppm and 1000 ppm. The application doses of potassium salt of phosphonic acid are generally between 1000 ppm and 20 000 ppm, particularly between 1000 ppm and 15 000 ppm.

According to a preferred aspect, the method of treatment according to the invention may consist of the simultaneous, separate or sequential application over time, of its ingredients.

The method according to the invention may consist of the application of a composition containing an essential oil or one or more terpene agent(s) contained, and/or mixtures thereof, on the one hand, and a composition containing a salt of phosphonic acid, on the other hand.

Alternatively, the method according to the invention may consist of applying a mixture containing an essential oil or one or more terpene agent(s) contained therein, and/or mixtures thereof, and a salt of phosphonic acid. In this case, the method may also include the preliminary step of preparing said mixture, comprising of the addition of a composition containing an essential oil or one or more terpene agent(s) contained therein, and/or mixtures thereof, on the one hand, to a composition containing a salt of phosphonic acid, on the other hand.

This step can be performed by mixing the two compositions in water, possibly in the optional presence of an emulsifier, followed by neutralisation by slow addition of the amount of base required to obtain the salt and/or pH desired.

The said mixture may also contain one or more organic solvents such as alcohols and/or one or more emulsifiers such as Tween 80.

Generally, the composition containing the phosphonic acid salt is an aqueous solution of the desired salt of the phosphite or an aqueous solution containing the phosphonic acid and the desired base at the required concentration. In this context one could indeed mention a concentrated aqueous solution of potassium sesquiphosphite at 750 g/l.

The composition containing the phosphonic acid is generally used at concentrations of between 0.1% and 1% by volume, that is to say between 0.1 litre and 1 litre of composition per 100 litres of water.

The composition containing an essential oil or one or more terpene agent(s) contained therein, and/or mixtures thereof may comprise, besides the essential oil or one or more terpene agent(s) contained therein, and/or mixtures thereof, one or more non ionic emulsifiers, lecithin, soybean oil.

In this context one could indeed mention the composition Bioxeda®, marketed by Xeda; this generally includes (percentage by weight):
clove oil: 20%
non ionic emulsifier: 18%
hydrolysed lecithin: 27%
soybean oil: 35%

The composition containing an essential oil or one or more terpene agent(s) contained therein, and/or mixtures thereof is generally used at concentrations of between 0.1% and 1% weight/volume, that is to say between 0.1 kg and 1 kg of composition per 100 litres of water, generally between 0.3% and 0.7% weight/volume.

In general one would apply between 3000 and 10 000 litres of treatment composition thus reconstituted at the concentrations indicated above for 100 to 300 tonnes of fruits or vegetables to be treated post-harvest and between 500 and 1000 litres/hectare of orchard.

Without being bound by theory, it would appear that the synergistic activity of the phosphonic acid salt and the essential oil or one or more terpene agent(s) contained therein, and/or mixtures thereof could be exercised by way of an immediate action controlling all fungal growth, and/or by the effect of partial salification of the phosphonic acid and for example by eugenol, leading to the formation of a mixed phosphite/eugenate salt of potassium which, by acting as a buffer solution, would slow down the rapid evaporation of the volatile product (eugenol) and thereby ensure the prolonged presence of the two active ingredients on the plant base.

The potential synergistic effect of the mixture may thus be linked to the limiting of the evaporation of the essential oil or one or more terpene agent(s) contained therein, and/or mixtures thereof, thus allowing the constant presence over time of the active substance on the treated plant.

The method according to the invention allows for the treatment of foodstuffs without leaving residues of synthetic organic products. It has a very broad spectrum of fungicidal and/or bactericidal activity. It also makes it possible to control the cold rot at fairly low concentrations, ensuring residue levels well below the limits for various different crops. Thus, the concentrations of phosphonic acid used by the method according to the invention make it possible to obtain residue levels of up to about ten times lower than the permissible limits.

The combination of two active ingredients does not give rise to resistant strains of fungi. Furthermore, the method according to the invention has a very low risk of environmental contamination, with the phosphonic acid being transformed into phosphate and the eugenol evaporating into the atmosphere.

The method according to the invention may also include the application one or more other pesticides such as fungicides, acaricides, insecticides or herbicides.

According to another aspect, the present invention also relates to compositions suitable for the method according to the invention.

Accordingly, the present invention relates to compositions containing phosphonic acid in an at least partially salified form, and an essential oil or one or more terpene agent(s) contained therein, and/or mixtures thereof.

The phosphonic acid salt may be prepared in advance or formed in situ within the treatment composition by reaction between phosphonic acid and the corresponding base, such as KOH, for example, the quantity of base being appropriate to the desired salt.

The invention therefore also relates to compositions containing phosphonic acid, a basic and an essential oil or one or more terpene agent(s) contained therein, and/or mixtures thereof.

In an unexpected manner, the compositions according to the invention remain clear and stable over time.

The combinations according to the invention have a temperature between 0° C. and 30° C.

Thus, the compositions generally comprise
between 10% and 60% by weight/volume of phosphonic acid salt,
between 1% and 20% by weight/volume of an essential oil or one or more terpene agent(s) contained therein, and/or mixtures thereof
in water.

More particularly:
between 10% and 20% by weight/volume of phosphonic acid, between 3% and 10% by weight/volume of an essential oil or one or more terpene agent(s) contained therein, and/or mixtures thereof and between 10% and 20% by weight/volume of base.

The compositions according to the invention may also contain a non ionic emulsifier, lecithin, soybean oil, one or more bases of water, one or more organic solvents such as alcohols and/or one or more emulsifiers such as Tween 80.

The compositions according to the invention may be prepared by mixing a concentrated solution of potassium sesquiphosphite at 750 g/l and a composition containing (weight %):
essential oil: 20%
non ionic emulsifier: 18%
hydrolysed lecithin: 27%
soybean oil: 35%

The compositions according to the invention may be prepared according to the method described here above for the preliminary step of the method according to the invention.

Generally, the pH of the compositions according to the invention is between 5 and 8, preferably between 6.2 and 7.4 and more preferably between 6.5 and 7.

More particularly, the present invention therefore also relates to a composition containing a salt of phosphonic acid, partially or totally salified, in an admixture with an essential oil or one or more terpene agent(s) contained therein, and/or non salified mixtures thereof, in aqueous solution, said composition having a pH between 5 and 8.

It is considered that a higher pH would lead to excessive loss of volatility of eugenol including the activity thereof partially by steam, as well as a phenomenon of phytotoxicity.

A lower pH would produce a rapid evaporation of terpene with loss of activity of the mixture.

The following are provided by way of illustrative and non limiting examples of the present invention.

EXAMPLES

Example 1

Activity of Combinations of Phosphonic Acid and Essential Oils (or Terpene Active Ingredients Thereof) at Ambient Temperature The efficacy of combinations of essential oils and potassium salt of phosphonic acid (potassium sesquiphosphite) to reduce the viability of fungal infection and diseases in potatoes during storage was measured in the following manner: the tubers were collected. 500 tubers were selected for their average infection of Rhizoctonia (variety Nicola Bio); Helminthosporium solani (variety Vivaldi traditional). The tubers were incubated at 15° C. for 45 days to allow the development of symptoms. 50 tubers (6 to 8 kg) were treated with a composition of essential oil (at 570 ppm or 1140 ppm), a composition of potassium salt of phosphonic acid at 0.6% or 1.2% by weight, as well as mixtures thereof. The phosphonic acid solution was sprayed at ambient temperature at an application rate of 75 mL per 5 kg. 50 mL of clove oil solution were sprayed out. The tubers were incubated at 8° C. for 45 days after treatment. The viability of colonies of Rhizoctonia and Helminthosporium was monitored. The results are summarised in the following table.

TABLE 1

| | Viability of Propagules (%) | |
|---|---|---|
| Treatment | Rhizoctonia | Helminthosporium solani |
| Control | 92 | 82 |
| 0.6% potassium sesquiphosphite | 60 | 30 |
| 1.2% potassium sesquiphosphite | 22 | 6 |
| 570 ppm clove oil | 64 | 40 |
| 570 ppm thymol | 75 | 45 |
| 570 ppm carvacrol | 52 | 50 |
| 570 ppm geraniol | 83 | 38 |
| 570 ppm clove oil + 0.6% potassium sesquiphosphite | 24 | 24 |
| 570 ppm clove oil + 1.2% potassium sesquiphosphite | 20 | 0 |
| 1140 ppm clove oil | 30 | 6 |
| 1140 ppm clove oil + 0.6% potassium sesquiphosphite | 6 | 0 |
| 1140 ppm clove oil + 1.2% potassium sesquiphosphite | 0 | 0 |
| 570 ppm thymol + 0.6% sesquiphosphite potassium | 18 | 16 |
| 570 ppm carvacrol + 0.6% Potassium sesquiphosphite | 15 | 22 |
| 570 ppm geraniol + 0.6% potassium sesquiphosphite | 26 | 16 |

The above results show that the phosphonic acid alone or an essential oil (or terpene active ingredient therein) alone control to an altogether insufficient degree the growth of Rhizoctonia or Helminthosporium solani. The combination of the two active agents however makes it possible to achieve full control of the growth of Helminthosporium at the lowest doses of oil and phosphonic acid. In similar fashion, the concentration at the highest doses of clove oil makes it possible in a fairly total manner, to inhibit the growth of Rhizoctonia, which is remarkable because this fungus is very difficult to control. These results are particularly unexpected because they enable the achievement of total control of a fungus after inoculation, an extremely rare result.

Example 2

Activity of a Combination of Phosphonic Acid and Clove Oil at Ambient Temperature on Citrus The efficicacy/selectivity of a composition of clove oil and potassium salt of phosphonic acid was evaluated against Geotrichum sp on citrus (orange and mandarin/tangerine).

The fruits were inoculated with a suspension of spores of Geotrichum sp after perforation of the skin. The application was carried out by spraying at ambient temperature in the case of the phosphonic acid alone or of the combination with clove oil. When clove oil alone was applied, the fruits were immersed for 2 min in a bath at a temperature of between 49° C. and 51° C. The fruits were stored. At various time intervals, the fruits were individually inspected for signs of phytotoxicity and efficacy by determining the percentage of the surface of the skin affected and the stage of development of the disease in the controls. The variables studied were the incidence (percentage of fruit affected) and severity of the attack (percentage of the fruit surface affected by the disease).

The treatments performed are summarised in the following table.

| Treatment | Formulation Conc. | Unit | Type | Active Ingredient | Dilution | Dose applied (weight active ingredient) | Conditions of application | Percentage of fruit affected after 14 days | Percentage of damage per fruit after 14 days |
|---|---|---|---|---|---|---|---|---|---|
| 1. Control untreated | | | | | | | | 12.5 (0.0%) | 0.37 (0.0%) |
| 2. Bioxeda | 180 | g/L | EC | Eugenol | 700 ml/ 100 L | 126 g/ 100 L | Immersion at 50° C. (2 min) | 15 (20%) | 0.32 (12.9%) |
| 3. K-Phos | 750 | g/L | SL | Potassium Sesquiphosphite | 500 ml/ 100 L | 375 g/ 100 L | Spraying at ambient temperature, | 14.78 (−18.2%) | 0.95 (−156.9%) |
| 4. Bioxeda | 180 | g/L | EC | Eugenol | 1500 ml/ 100 L | 270 g/ 100 L | | 2.5 (80%) | 0.03 (91 6%) |
| K-Phos | 750 | g/L | SL | Potassium Sesquiphosphite | 500 ml/ 100 L | 375 g/ 100 L | | | |

EC: Emulsifiable Concentrate
SL: Soluble Concentrate

The results in the table here above obtained for the mandarin ortanique variety compare untreated control fruits to the fruits treated with clove oil alone applied at 50° C., the fruits treated with potassium salt of phosphonic acid alone and the fruits treated at ambient temperature with the combination of the two compositions.

Following the 14 days of treatment, the application of clove oil alone and of the potassium salt of phosphonic acid alone showed no activity. However, the combination of the two compositions yielded 80% activity compared to the control. This phenomenon was even more pronounced with regard to the analysis of the surface of infected fruits where no control of fungal growth was obtained with the individual treatment, whereas the mixture made it possible to achieve 91.6% of control.

Example 3

Activity of a Combination of Phosphonic Acid and Clove Oil at Ambient Temperature on Olive Trees Affected by *Colletotrichum gloeosporioides*

This fungus strongly attacks olive orchards (about 70% olive plants are attacked by this fungus in Spain).

The control of this disease is virtually nonexistent, the only treatments showing a low level of activity being copper treatments, with Bordeaux mixture and Captan. A composition at about 20% of clove oil and a composition of the potassium salt of phosphonic acid were separately applied at doses of 0.3% and 0.5% respectively, as well as in combination with the same doses.

The results are summarised in the following table.

| | Percentage of olive leaves with symptoms of infection | |
|---|---|---|
| | t1 | t1 + 90 days |
| Control | 36.5% | 54% |
| 0.3% clove oil (at 20%) | 31% | 42% |
| 0 5% potassium sesquiphosphite | 41% | 50% |
| 0.3% clove oil (at 20%) + 0.5% potassium sesquiphosphite 750 g/l | 14% | 12% |

The results in the above table show that the application of clove oil alone or phosphonic acid alone shows only a low level of activity compared to the control, with, moreover, a tendency to a gradual increase in the percentage of infection over time, alongside the untreated control. In contrast, the mixture of both products showed a very significant reduction of infection (approximately 3 times higher than in the phosphonic acid alone), as well as a tendency to decrease the rate of infection after repeated applications of the treatment.

The overall results here above demonstrate the synergy between clove oil and the potassium salt of phosphonic acid at ambient temperature.

Example 4

Preparation of a Composition According to the Invention

A mixture is made containing water, eugenol, isopropanol, and the emulsifier to which is added the calculated quantity of phosphonic acid. This is then neutralised by slowly adding in small incremental amounts of potassium hydroxide to the point of desired salification corresponding to a pH of 6.8 of the solution of the mixture at 1% in water.

The invention claimed is:

1. A method for the pre or post harvest treatment of plant products that comprises the application of:
    an at least partially salified form of phosphonic acid having the general formula $H_xM_yPO_3$, wherein M represents a member of the group consisting of an alkali metal, alkaline earth metal, ammonium group, or amino group, X is between 1 and 2, Y is between 1 and 2, and x +y=3, and
    an essential oil or one or more terpene agent(s) contained therein wherein the essential oil is selected from the group consisting of clove oil, thyme oil, oregano oil, cinnamon oil, and peppermint oil, and wherein the one or more terpene agent(s) contained therein is selected from the group consisting of eugenol, isoeugenol, L-carvone, thymol, geraniol, carvacrol, cinnamaldehyde and mixtures thereof,
    at a temperature of between 0° C. and 30° C.
2. A method according to claim 1, such that the salt has the formula $H_{1.5}M_{1.5}PO_3$ with M=potassium.

3. A method according to claim 1 such that the phosphonic acid salt is prepared in advance or formed in situ within the treatment composition, in the presence of the corresponding base.

4. A method according to claim 1 consisting of the application of:
phosphonic acid,
a base and
the essential oil or one or more terpene agent(s) contained therein, and/or mixtures thereof,
at ambient temperature.

5. A method according to claim 1 for fungicidal and/or bactericidal treatment.

6. A method according to claim 1 for the treatment of *Phytophtora, Monilia, Penicillium* sp, *Geotrichum* sp, *Rhizoctonia, Helminthosporium, Cholletotrichum.*

7. A method according to claim 1 carried out by way of spraying.

8. A method according to claim 1 carried out in the orchard.

9. A method according to claim 1 such that the doses for application of essential oil or one or more terpene agent(s) contained therein, and/or mixtures thereof are between 300 ppm and 4500 ppm and the doses for application of potassium salt of the phosphonic acid are between 1000 ppm and 20 000 ppm.

10. A method according to claim 1 comprising the simultaneous, separate or sequential application over time, of the ingredients.

11. A method according to claim 1 further comprising the preliminary step of preparing said mixture of ingredients by the addition of a composition containing the essential oil or one or more terpene agent(s) contained therein, and/or mixtures thereof, on the one hand, to a composition containing a salt of phosphonic acid, on the other hand.

12. A method according to claim 11 such that the composition containing the salt of the phosphonic acid is a concentrated aqueous solution of potassium sesquiphosphite at 750 g/l.

13. A method according to claim 11 such that the composition containing an essential oil or one or more terpene agent(s) contained therein, and/or mixtures thereof consists of (percentage by weight):
clove oil: 20%
non ionic emulsifier: 18%
hydrolysed lecithin: 27%
soybean oil: 35%.

14. A method according to claim 1 consisting of the application of one or more other phytosanitary plant protection products.

15. A composition at a temperature of between 0° C. and 30° C. containing phosphonic acid in an at least partially salified form having the general formula $H_xM_yPO_3$, wherein M represents a member of the group consisting of an alkali metal, alkaline earth metal, ammonium group, or amino group, X is between 1 and 2, Y is between 1 and 2, and x+y=3, an essential oil or one or more terpene agent(s) contained therein, and/or mixtures thereof, and at least one from among a non-ionic emulsifier, lecithin, soybean oil, an inorganic base, an organic base, water, one or more organic solvent and one or more emulsifiers.

16. A composition according to claim 15 containing:
between 10% and 60% by weight/volume of phosphonic acid salt,
between 1% and 20% by weight/volume of an essential oil or one or more terpene agent(s) contained therein, and/or mixtures thereof,
in water.

17. A composition according to claim 15 such that its pH is between 5 and 8.

18. A composition according to claim 15, such that the phosphonic acid salt has the formula $H_{1.5}M_{1.5}PO_3$ with M=potassium.

* * * * *